United States Patent [19]  
Fukuoka et al.

[11] Patent Number: 5,011,950  
[45] Date of Patent: Apr. 30, 1991

[54] AROMATIC AMINE DERIVATIVES

[75] Inventors: Daisuke Fukuoka, Iwakuni; Katsuya Takahashi, Ohtake; Isao Hashimoto, Iwakuni, all of Japan

[73] Assignee: Mitsui Petrochemical Industries, Ltd., Tokyo, Japan

[21] Appl. No.: 151,594

[22] Filed: Feb. 2, 1988

[30] Foreign Application Priority Data

Feb. 5, 1987 [JP] Japan ................. 62-23553

[51] Int. Cl.$^5$ ........................... C07D 307/80
[52] U.S. Cl. ..................... 549/336; 549/445; 549/462; 549/466; 549/400; 549/398; 549/437; 549/434; 549/458; 549/386; 549/334; 549/387; 549/464; 549/331; 71/88; 71/94
[58] Field of Search ............ 549/445, 460, 458, 466, 549/462, 464, 334, 333, 336, 331, 387, 386, 399, 398, 385, 400, 408, 437, 434; 71/88

[56] References Cited

U.S. PATENT DOCUMENTS 4,120,871 10/1978 Gates et al. .............. 549/310  
4,426,385 1/1984 Cain ....................... 546/269  
4,521,426 6/1985 Cain ....................... 546/297

FOREIGN PATENT DOCUMENTS 0059884 9/1982 European Pat. Off. .  
0118794 9/1984 European Pat. Off. .  
2734148 3/1980 Fed. Rep. of Germany .  
1192002 5/1970 United Kingdom .

OTHER PUBLICATIONS

Chemical Abstracts, vol. 98, No. 1, p. 250, 98:2740p, Jan. 3, 1983.  
Chemical Abstracts, vol. 81, No. 8, p. 2, 37845c, Aug. 26, 1974.  
European Search Report dated May 24, 1988.  
Matsumoto et al., CA 107:175872r.  
Takematsu et al., CA 107:236509b.

Primary Examiner—Jane T. Fan  
Attorney, Agent, or Firm—Sherman and Shalloway

[57] ABSTRACT

Novel aromatic amine derivatives of specific structure are useful intermediates for herbicides. The aromatic amine compounds have the structure shown by formula [I]:

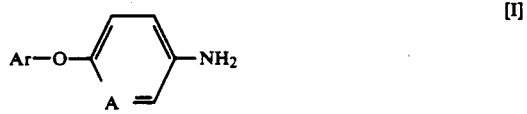

wherein Ar and A are as defined herein.

1 Claim, No Drawings

AROMATIC AMINE DERIVATIVES

BACKGROUND OF THE INVENTION

This invention relates to novel aromatic amine derivatives.

Wheat, corn, rice, and soybean plants are important crops. A variety of herbicides have been applied in order to increase the crop fields. Prior art herbicides are not satisfactory in herbicidal activity and safety to growing crops. There is a need for a safe herbicide which can control weeds at a low level of application while giving no or little phytotoxity to growing crops.

During our search to produce a herbicide which is applicable in a small amount to kill weeds without phytotoxity to growing crops, we have discovered novel aromatic amine derivatives which are useful as intermediates for herbicides meeting the above requirements.

SUMMARY OF THE INVENTION

An object of the present invention is to provide novel aromatic amine derivatives which are useful as intermediates for herbicides.

According to the present invention, there is provided a novel aromatic amine derivative of the general formula [I]:

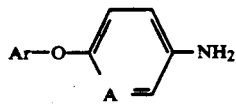

[I]

wherein Ar is a radical selected from the group consisting of

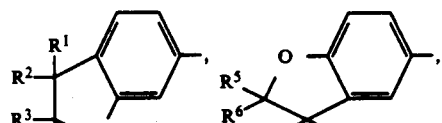

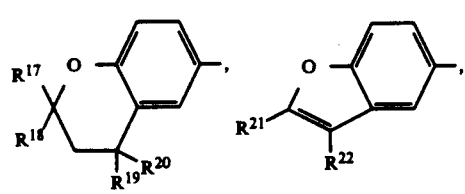

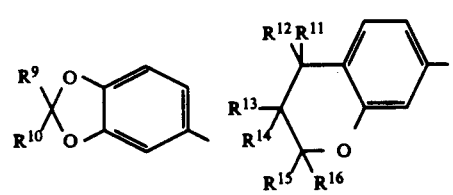

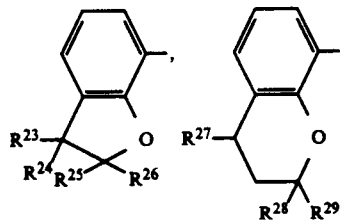

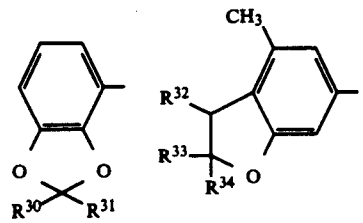

and

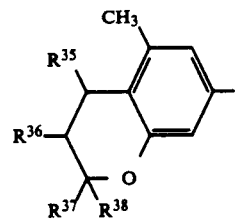

wherein $R^1$ to $R^{15}$ and $R^{17}$ to $R^{38}$ may be the same or different and are independently selected from the group consisting of hydrogen, lower alkyl radicals, and lower alkoxyl radicals, $R^{16}$ is selected from the group consisting of hydrogen, lower alkyl radicals, lower alkoxyl radicals and hydroxyl, with the proviso that $R^2$ and $R^3$, $R^6$ and $R^7$, $R^9$ and $R^{10}$, $R^{11}$ and $R^{15}$, or $R^{15}$ and $R^{16}$ may, taken together, represent an alkylene chain, which may be substituted with a lower alkyl radical, to form a 5- or 6-membered ring with the carbon atoms to which they are attached, $R^{11}$ and $R^{12}$ may, taken together, represent an ethylene dioxyl radical, or $R^{14}$ and $R^{15}$ may, taken together, represent a dichloromethylene radical; and A is a nitrogen atom or

wherein X is selected from the group consisting of a hydrogen atom, a chlorine atom, a nitro radical, and a trifluoromethyl radical, when both $R^5$ and $R^6$ are methyl radicals and A is

at least one of $R^7$ and $R^8$ does not represent hydrogen atom, when both $R^{25}$ and $R^{26}$ are methyl radicals and A is

at least one of $R^{23}$ and $R^{24}$ does not represent hydrogen atom.

DETAILED DESCRIPTION OF THE INVENTION

The aromatic amine derivatives of the present invention have the general formula [I] as defined above.

Examples of the lower alkyl radicals represented by $R^1$ through $R^{38}$ include methyl, ethyl, n-propyl, isopropyl, n-butyl, isobutyl, sec-butyl, tert-butyl, etc. Examples of the lower alkoxyl radicals represented by $R^1$ through $R^{38}$ include methoxy, ethoxy, n-propoxy, isopropoxy, n-butoxy, isobutoxy, sec-butoxy, etc.

Examples of the radicals represented by Ar are shown below.

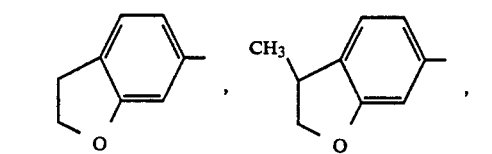

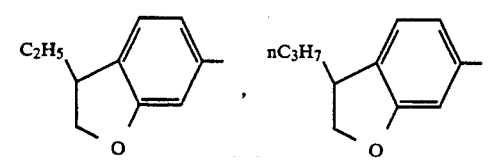

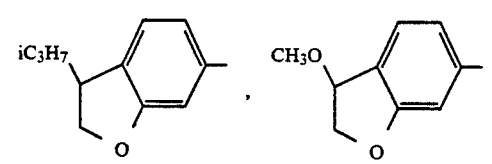

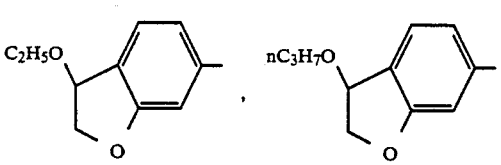

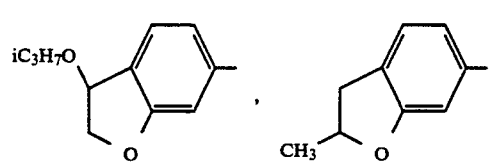

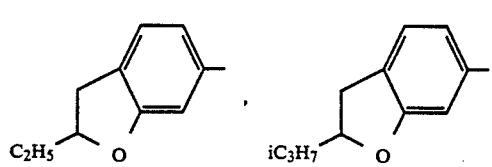

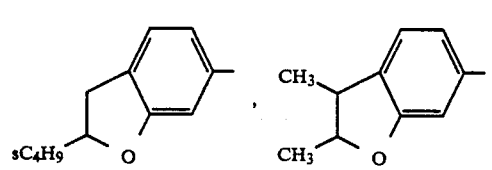

-continued

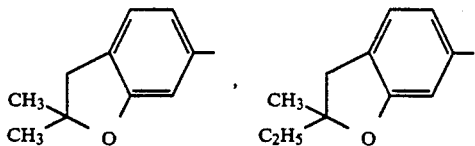

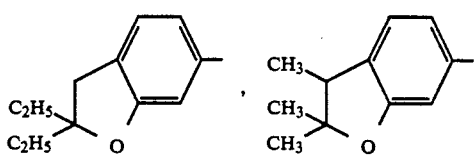

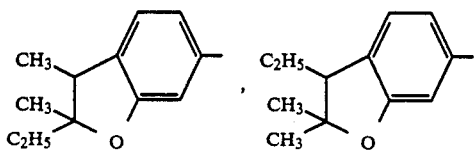

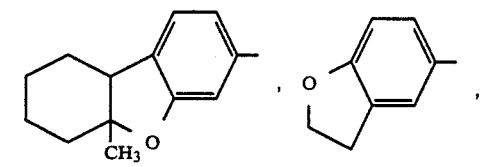

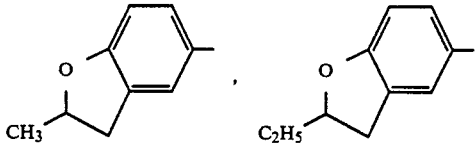

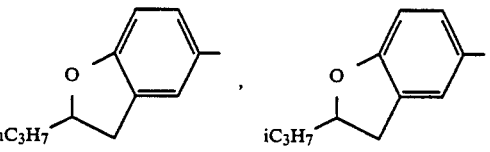

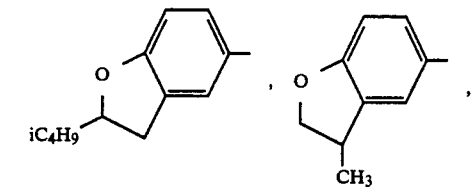

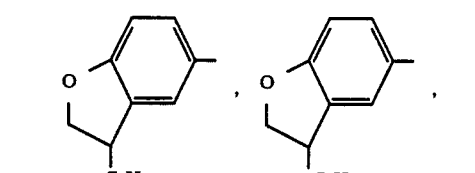

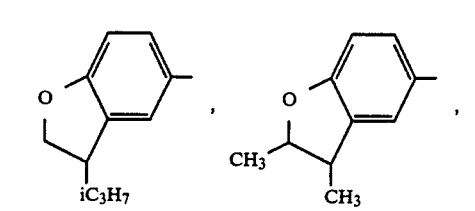

-continued
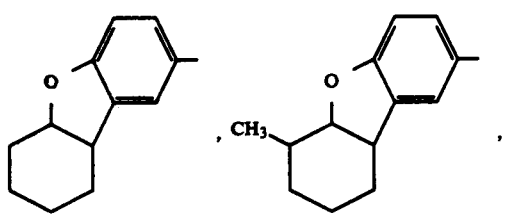
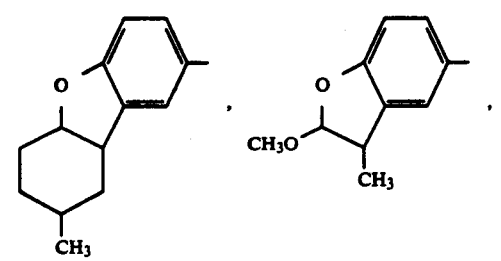
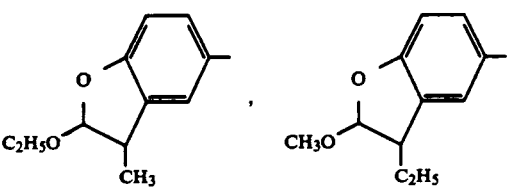
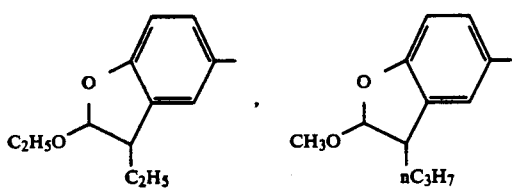
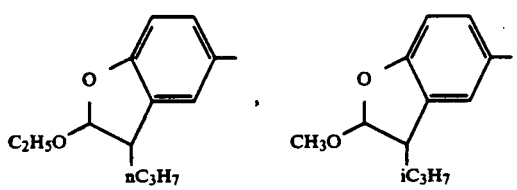
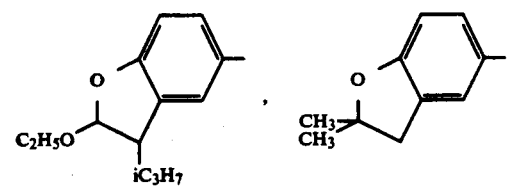
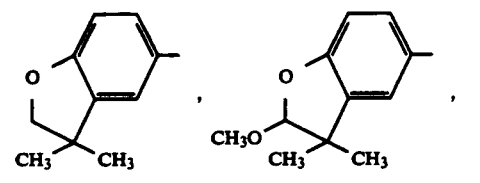
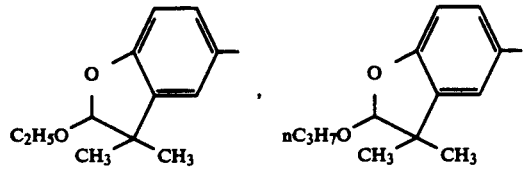
-continued
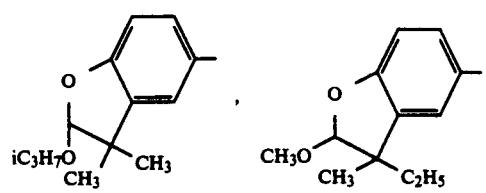
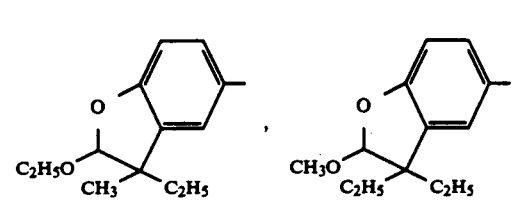
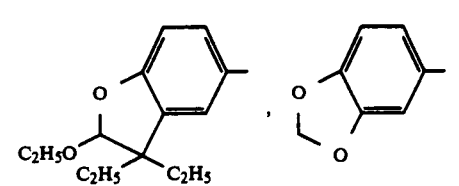
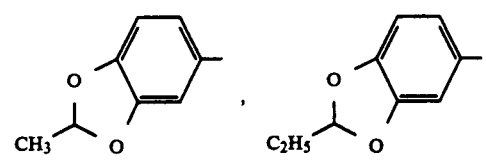
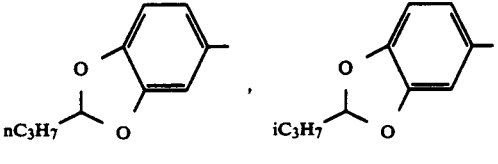
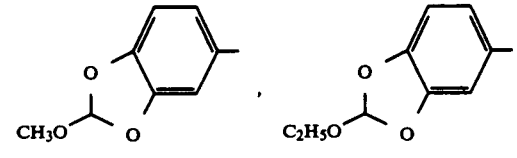
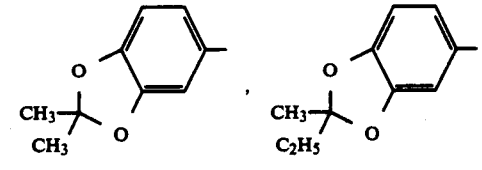
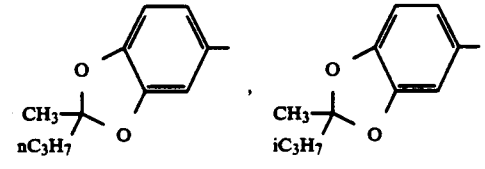
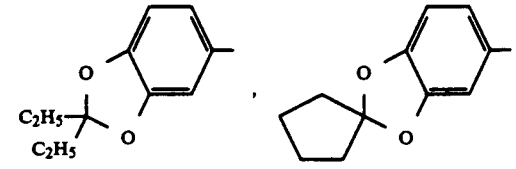

-continued
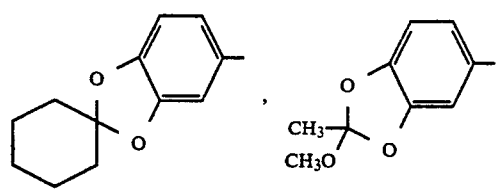 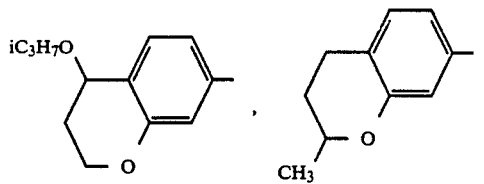
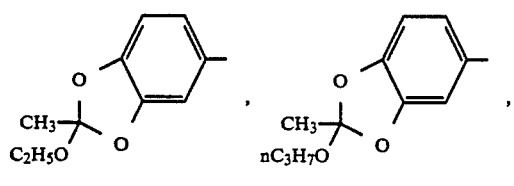 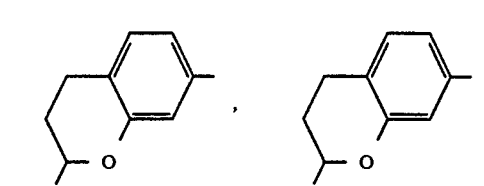
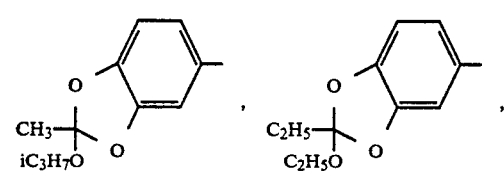 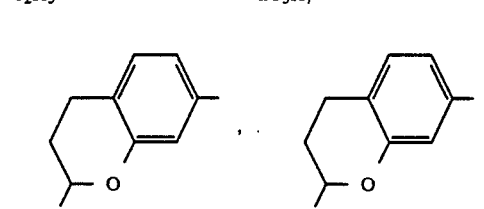
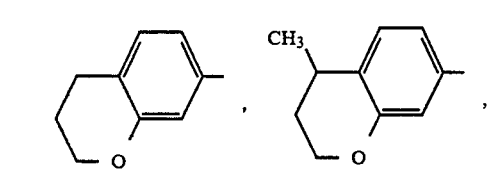 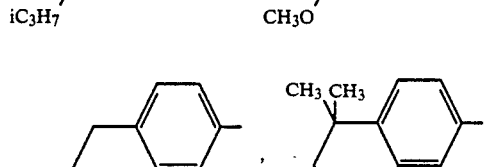
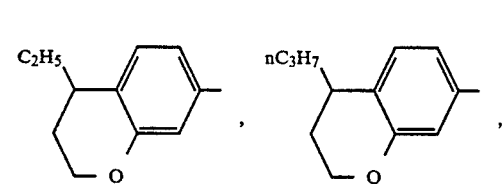 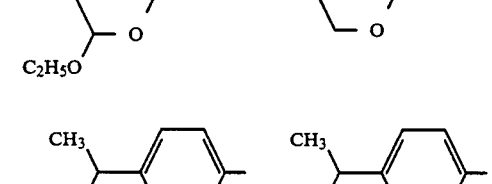
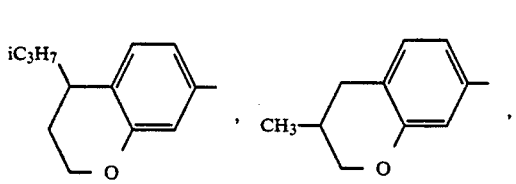 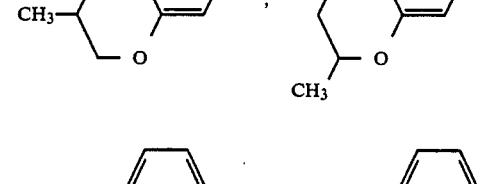
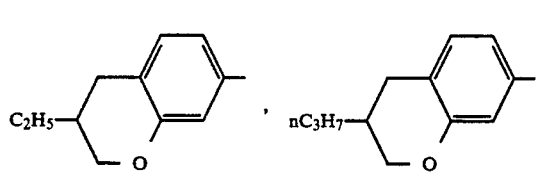 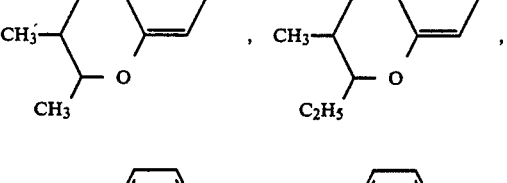
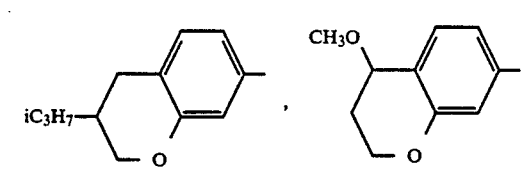 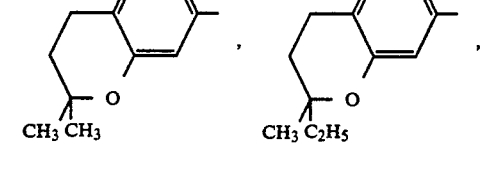
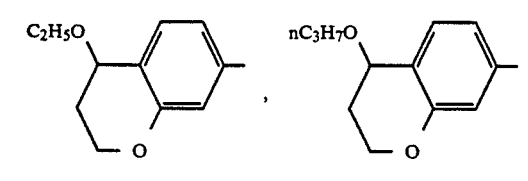 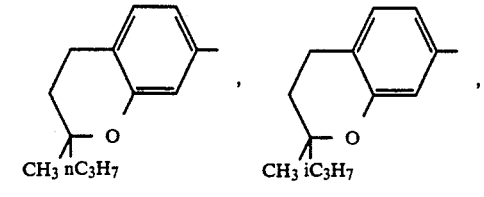

-continued
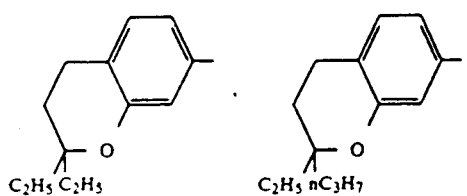
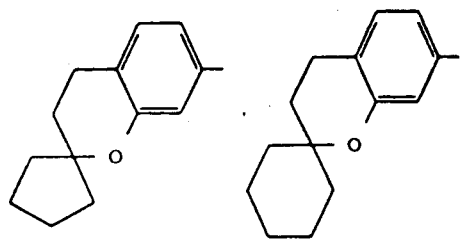
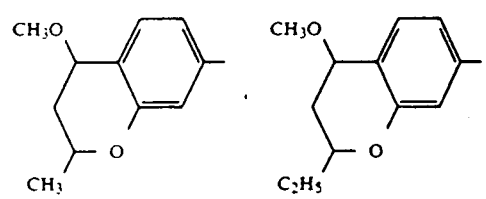
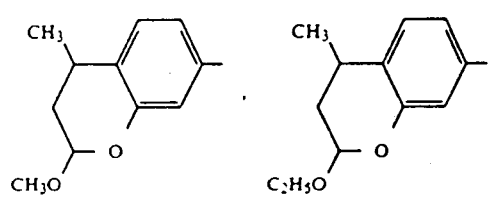
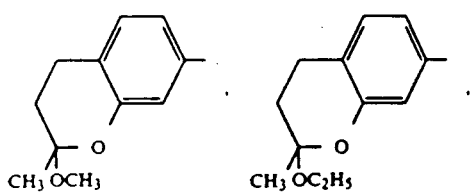
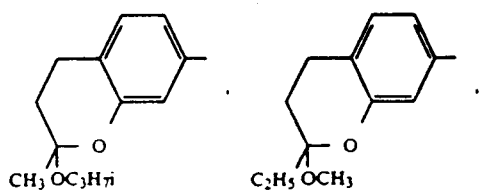
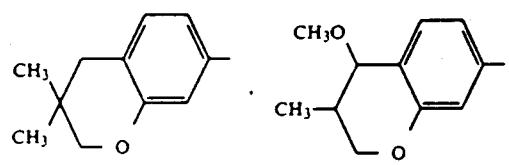
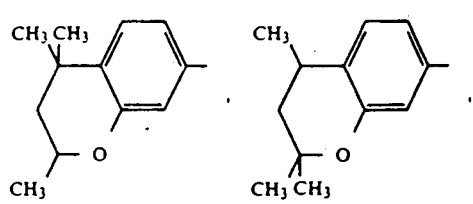
-continued
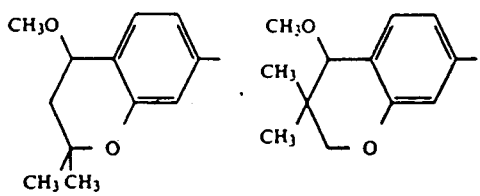
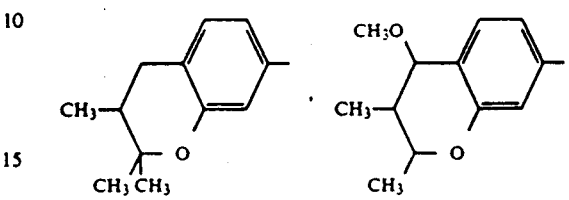
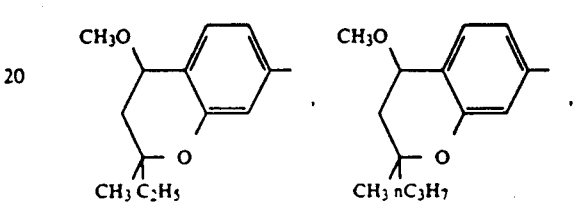
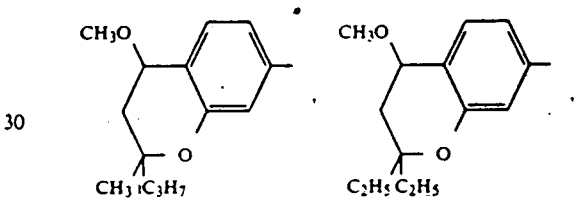
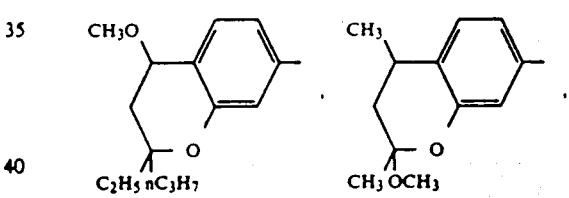
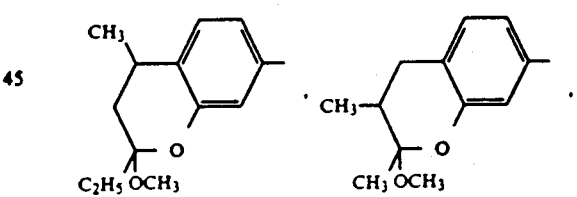
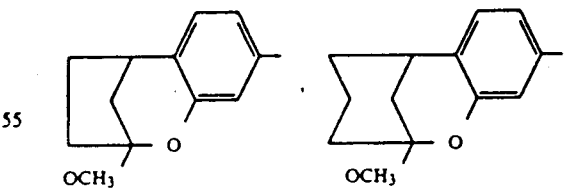
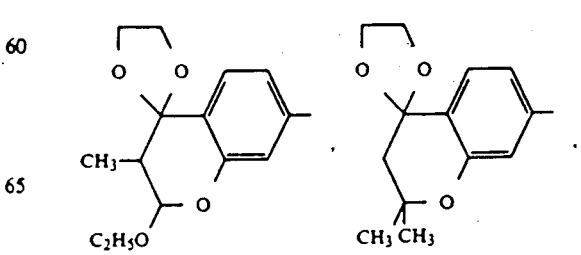

-continued
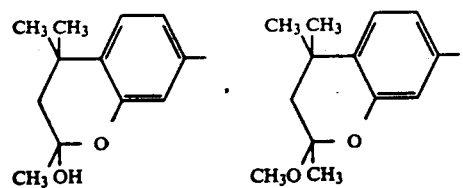
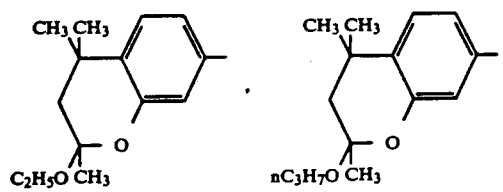
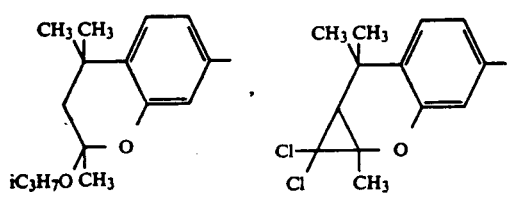
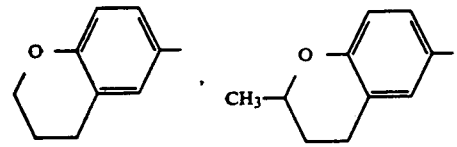
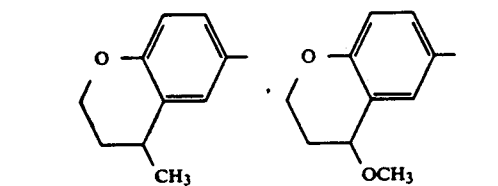
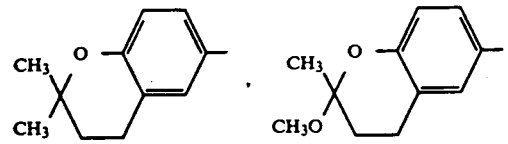
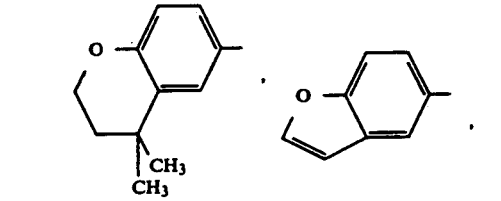
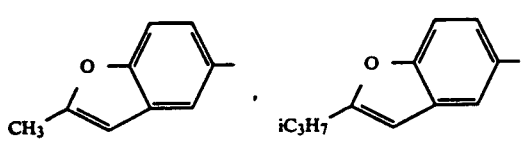
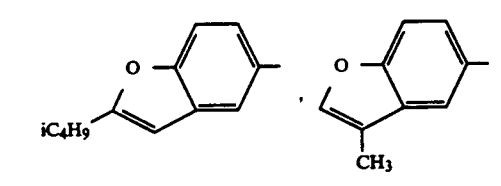
-continued
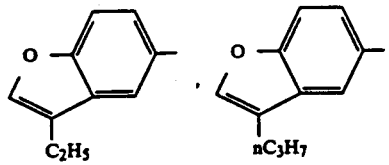
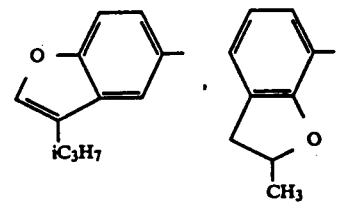
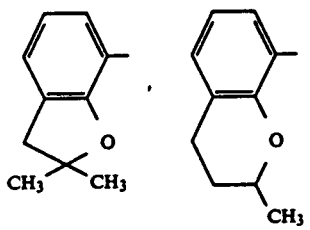
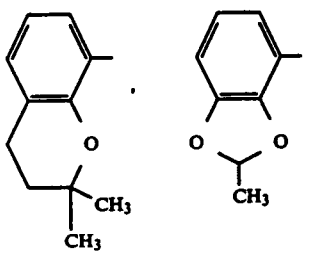
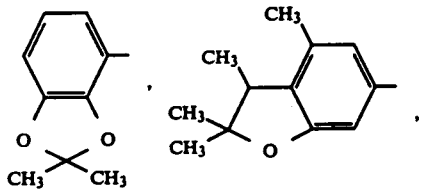
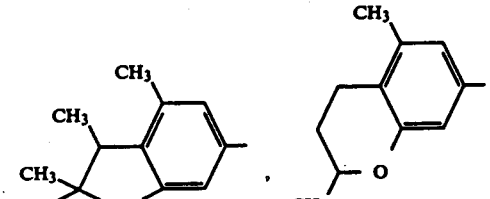
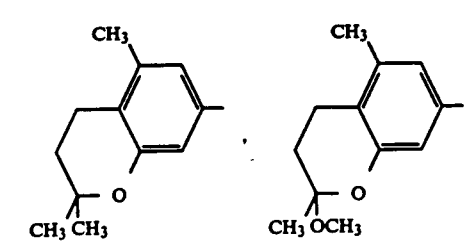

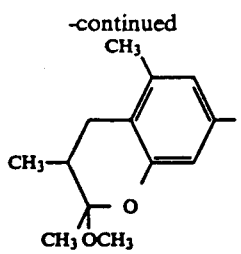

Preferred examples of the aromatic amine derivatives of the present invention are shown in Tables 1 through 11. Particularly preferred examples of the aromatic amine derivatives of the present invention are compounds shown in Tables 1, 3, 4, 5, 6, 8, 9, 10 and 11.

TABLE 1

| Compound No. | $R^1$ | $R^2$ | $R^3$ | $R^4$ | A |
|---|---|---|---|---|---|
| 1 | $CH_3$ | H | H | H | 3-pyridyl |
| 2 | $CH_3$ | H | H | H | phenyl |
| 3 | $CH_3$ | H | $CH_3$ | $CH_3$ | 3-pyridyl |
| 4 | $CH_3$ | H | $CH_3$ | $CH_3$ | phenyl |
| 5 | H | H | H | H | phenyl |
| 6 | $C_2H_5$ | H | H | H | phenyl |
| 7 | $C_3H_7^n$ | H | H | H | phenyl |
| 8 | $CH_3$ | H | $CH_3$ | H | phenyl |
| 9 | H | H | $CH_3$ | H | phenyl |
| 10 | H | H | $C_2H_5$ | H | phenyl |
| 11 | H | H | $C_3H_7^i$ | H | phenyl |
| 12 | H | H | $C_4H_9^t$ | H | phenyl |
| 13 | H | H | $CH_3$ | $CH_3$ | phenyl |
| 14 | H | H | $CH_3$ | $C_2H_5$ | phenyl |
| 15 | H | H | $C_2H_5$ | $C_2H_5$ | phenyl |
| 16 | $CH_3$ | H | $CH_3$ | $C_2H_5$ | 3-pyridyl |
| 17 | $CH_3$ | H | $CH_3$ | $C_2H_5$ | phenyl |
| 18 | $CH_3$ | H | $CH_3$ | $C_2H_5$ | 3-Cl-phenyl |

TABLE 1-continued

| Compound No. | R¹ | R² | R³ | R⁴ | A |
|---|---|---|---|---|---|
| 19 | $CH_3$ | H | $CH_3$ | $C_2H_5$ | (phenyl with $NO_2$) |
| 20 | $CH_3$ | H | $CH_3$ | $C_2H_5$ | (phenyl with $CF_3$) |
| 21 | $C_2H_5$ | H | $CH_3$ | $CH_3$ | (phenyl) |
| 22 | H | $-(CH_2)_4-$ | | $CH_3$ | (phenyl) |

TABLE 2

| Compound No. | R⁵ | R⁶ | R⁷ | R⁸ | A |
|---|---|---|---|---|---|
| 23 | $CH_3$ | H | H | H | (pyridyl) |
| 24 | $CH_3$ | H | H | H | (phenyl) |
| 25 | H | H | $CH_3$ | H | (phenyl) |

TABLE 2-continued

| Compound No. | R⁵ | R⁶ | R⁷ | R⁸ | A |
|---|---|---|---|---|---|
| 26 | H | H | $C_2H_5$ | H | (phenyl) |
| 27 | H | H | $C_3H_7{}^n$ | H | (phenyl) |
| 28 | H | H | $C_3H_7{}^i$ | H | (phenyl) |
| 29 | $C_3H_7{}^i$ | H | H | H | (phenyl) |
| 30 | $OCH_3$ | H | $C_2H_5$ | H | (phenyl) |
| 31 | $CH_3$ | H | $CH_3$ | H | (pyridyl) |
| 32 | $CH_3$ | H | $CH_3$ | H | (phenyl) |
| 33 | $CH_3$ | $CH_3$ | H | H | (pyridyl) |
| 35 | H | H | $CH_3$ | $CH_3$ | (phenyl) |
| 36 | $OC_2H_5$ | H | $CH_3$ | H | (phenyl) |
| 37 | $OCH_3$ | H | $CH_3$ | $CH_3$ | (pyridyl) |

TABLE 2-continued

Structure: benzofuran (with R⁵, R⁶ on one ring carbon and R⁷, R⁸ on adjacent carbon) linked via –O– to pyridine bearing –NH₂, where the pyridine is further connected to group A.

| Compound No. | $R^5$ | $R^6$ | $R^7$ | $R^8$ | A |
|---|---|---|---|---|---|
| 38 | OCH₃ | H | CH₃ | CH₃ | phenylene |
| 39 | OCH₃ | H | CH₃ | CH₃ | 3-chloro-phenylene |
| 40 | OCH₃ | H | CH₃ | C₂H₅ | phenylene |
| 41 | OCH₃ | H | C₂H₅ | C₂H₅ | phenylene |
| 42 | OCH₃ | H | C₃H₇$^i$ | H | phenylene |
| 43 | OC₂H₅ | H | C₂H₅ | H | phenylene |
| 44 | OC₂H₅ | H | C₃H₇$^i$ | H | phenylene |
| 45 | OC₂H₅ | H | CH₃ | CH₃ | phenylene |
| 46 | OC₃H₇$^i$ | H | CH₃ | CH₃ | cyclohexylene |
| 47 | H | —(CH₂)₄— | | H | phenylene |
| 48 | H | —CH(CH₃)—(CH₂)₃— | | H | phenylene |
| 49 | H | —(CH₂)₂—CH(CH₃)—CH₂— | | H | phenylene |

TABLE 3

Structure: 1,3-benzodioxole (with R⁹, R¹⁰ on the acetal carbon) linked via –O– to pyridine bearing –NH₂, connected to group A.

| Compound No. | $R^9$ | $R^{10}$ | A |
|---|---|---|---|
| 50 | H | H | phenylene |
| 51 | C₂H₅ | CH₃ | phenylene |
| 52 | CH₃ | CH₃ | pyridylene |
| 53 | CH₃ | CH₃ | phenylene |
| 54 | OCH₃ | CH₃ | phenylene |
| 55 | OC₂H₅ | CH₃ | phenylene |
| 56 | OC₂H₅ | C₂H₅ | phenylene |

TABLE 3-continued
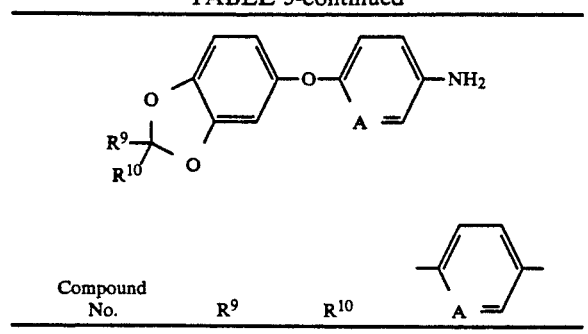
| Compound No. | $R^9$ | $R^{10}$ | A |
|---|---|---|---|
| 57 | $OCH_3$ | H | (3,6-substituted phenyl) |
| 58 | $OC_2H_5$ | H | (1,4-phenylene) |
| 59 | $CH_3$ | $C_3H_7^i$ | (1,4-phenylene) |
| 60 | $C_2H_5$ | $C_2H_5$ | (1,4-phenylene) |
| 61 | $-(CH_2)_4-$ | | (1,4-phenylene) |
TABLE 4
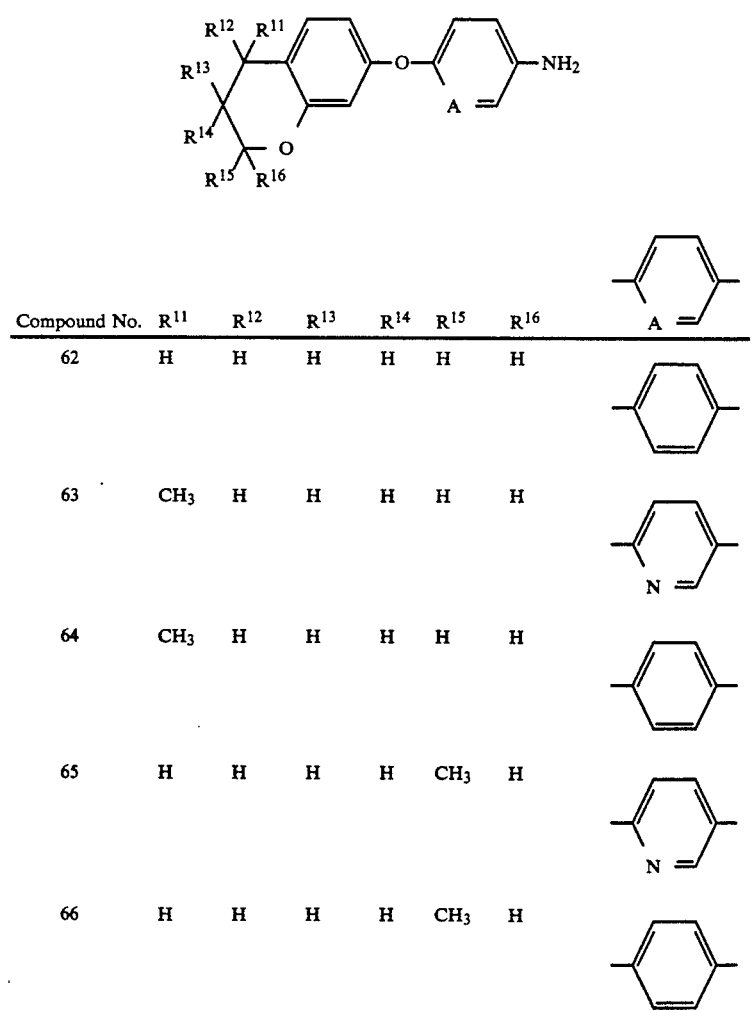
| Compound No. | $R^{11}$ | $R^{12}$ | $R^{13}$ | $R^{14}$ | $R^{15}$ | $R^{16}$ | A |
|---|---|---|---|---|---|---|---|
| 62 | H | H | H | H | H | H | (1,4-phenylene) |
| 63 | $CH_3$ | H | H | H | H | H | (2,5-pyridyl) |
| 64 | $CH_3$ | H | H | H | H | H | (1,4-phenylene) |
| 65 | H | H | H | H | $CH_3$ | H | (2,5-pyridyl) |
| 66 | H | H | H | H | $CH_3$ | H | (1,4-phenylene) |

TABLE 4-continued
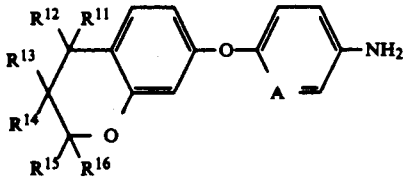
| Compound No. | R¹¹ | R¹² | R¹³ | R¹⁴ | R¹⁵ | R¹⁶ | A |
|---|---|---|---|---|---|---|---|
| 67 | CH₃ | CH₃ | H | H | H | H | 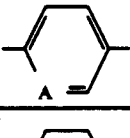 |
| 68 | H | H | H | H | CH₃ | CH₃ | 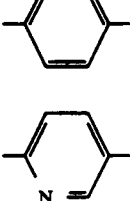 |
| 69 | H | H | H | H | CH₃ | CH₃ | 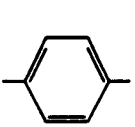 |
| 70 | H | H | H | H | CH₃ | CH₃ | 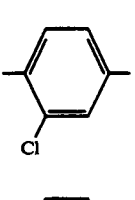 |
| 71 | H | H | H | H | CH₃ | CH₃ | 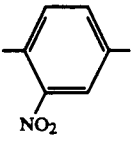 |
| 72 | H | H | H | H | CH₃ | CH₃ | 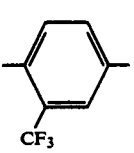 |
| 73 | CH₃ | CH₃ | H | H | CH₃ | H | 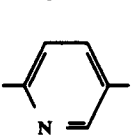 |
| 74 | CH₃ | CH₃ | H | H | CH₃ | H |  |
| 75 | CH₃ | H | H | H | CH₃ | CH₃ | 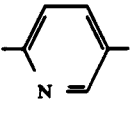 |
| 76 | CH₃ | H | H | H | CH₃ | CH₃ | 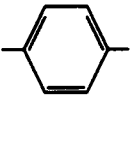 |

TABLE 4-continued

| Compound No. | R11 | R12 | R13 | R14 | R15 | R16 | A |
|---|---|---|---|---|---|---|---|
| 77 | OCH3 | H | H | H | CH3 | CH3 | para-phenylene |
| 78 | CH3 | CH3 | H | H | CH3 | OCH3 | para-phenylene |
| 79 | CH3 | CH3 | H | H | CH3 | OCH3 | pyridine-2,5-diyl |
| 80 | CH3 | CH3 | H | H | CH3 | OCH3 | para-phenylene |
| 81 | CH3 | CH3 | H | H | CH3 | OCH3 | 2-chloro-para-phenylene |
| 82 | CH3 | CH3 | H | H | CH3 | OCH3 | 2-nitro-para-phenylene |
| 83 | CH3 | CH3 | H | H | CH3 | OC2H5 | 2-trifluoromethyl-para-phenylene |
| 84 | CH3 | CH3 | H | H | CH3 | OC3H7$^n$ | para-phenylene |
| 85 | CH3 | CH3 | H | H | CH3 | OC3H7$^i$ | para-phenylene |
| 86 | OCH3 | H | H | H | H | H | para-phenylene |

TABLE 4-continued
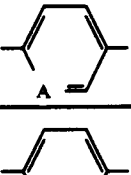
| Compound No. | R11 | R12 | R13 | R14 | R15 | R16 | A |
|---|---|---|---|---|---|---|---|
| 87 | H | H | H | H | C2H5 | H |  |
| 88 | H | H | H | H | C3H7i | H |  |
| 89 | H | H | H | H | OCH3 | H |  |
| 90 | H | H | H | H | OC2H5 | H |  |
| 91 | C2H5 | H | H | H | H | H |  |
| 92 | CH3 | H | CH3 | H | H | H |  |
| 93 | CH3 | H | H | H | CH3 | H |  |
| 94 | CH3 | H | H | H | OCH3 | H |  |
| 95 | CH3 | H | H | H | OC2H5 | H |  |
| 96 | OCH3 | H | H | H | CH3 | H |  |
| 97 | OCH3 | H | H | H | C2H5 | H | |

TABLE 4-continued
| Compound No. | $R^{11}$ | $R^{12}$ | $R^{13}$ | $R^{14}$ | $R^{15}$ | $R^{16}$ | A |
|---|---|---|---|---|---|---|---|
| 98 | H | H | $CH_3$ | H | $CH_3$ | H | 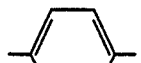 |
| 99 | H | H | $CH_3$ | H | $C_2H_5$ | H | 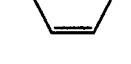 |
| 100 | H | H | H | H | $CH_3$ | $C_2H_5$ | 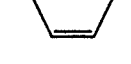 |
| 101 | H | H | H | H | $CH_3$ | $C_3H_7{}^n$ |  |
| 102 | H | H | H | H | $CH_3$ | $C_3H_7{}^i$ | 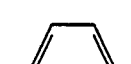 |
| 103 | H | H | H | H | $C_2H_5$ | $C_2H_5$ | 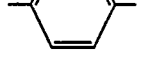 |
| 104 | H | H | H | H | $C_2H_5$ | $C_3H_7{}^n$ |  |
| 105 | H | H | H | H | —$(CH_2)_5$— | | 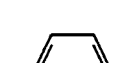 |
| 106 | H | H | H | H | $CH_3$ | $OCH_3$ |  |
| 107 | H | H | H | H | $CH_3$ | $OC_2H_5$ |  |
| 108 | H | H | H | H | $CH_3$ | $OC_3H_7{}^i$ | 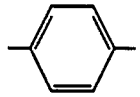 |

TABLE 4-continued

Structure:
$R^{12}, R^{11}$ on carbon attached to phenyl ring; $R^{13}$ on next carbon; $R^{14}$ on next carbon; $R^{15}, R^{16}$ on carbon attached to O. The phenyl ring bearing the alkyl chain is connected via O to ring A, which bears $NH_2$.

| Compound No. | $R^{11}$ | $R^{12}$ | $R^{13}$ | $R^{14}$ | $R^{15}$ | $R^{16}$ | A |
|---|---|---|---|---|---|---|---|
| 109 | H | H | H | H | $C_2H_5$ | $OCH_3$ | phenylene |
| 110 | $CH_3$ | H | H | H | $CH_3$ | $OCH_3$ | phenylene |
| 111 | $CH_3$ | H | H | H | $C_2H_5$ | $OCH_3$ | phenylene |
| 112 | $OCH_3$ | H | $CH_3$ | H | $CH_3$ | H | phenylene |
| 113 | H | H | $CH_3$ | H | $CH_3$ | $CH_3$ | phenylene |
| 114 | H | H | $CH_3$ | H | $CH_3$ | $OCH_3$ | phenylene |
| 115 | $OCH_3$ | H | H | H | $CH_3$ | $C_2H_5$ | phenylene |
| 116 | $OCH_3$ | H | H | H | $CH_3$ | $C_3H_7^i$ | phenylene |
| 117 | $OCH_3$ | H | H | H | $C_2H_5$ | $C_2H_5$ | phenylene |
| 118 | $OCH_3$ | H | H | H | $C_2H_5$ | $C_3H_7^n$ | phenylene |
| 119 | —O(CH$_2$)$_2$O— | | H | H | $CH_3$ | H | phenylene |

TABLE 4-continued

*[Structure: phenyl ring with R11, R12, R13, R14, R15, R16 substituents and O in ring, connected via ether to phenyl-A-NH2]*

| Compound No. | R11 | R12 | R13 | R14 | R15 | R16 | A |
|---|---|---|---|---|---|---|---|
| 120 | —O(CH$_2$)$_2$O— | | H | H | C$_2$H$_5$ | H | para-phenylene |
| 121 | —O(CH$_2$)$_2$O— | | H | H | C$_3$H$_7^i$ | H | para-phenylene |
| 122 | —O(CH$_2$)$_2$O— | | CH$_3$ | H | CH$_3$ | H | para-phenylene |
| 123 | —O(CH$_2$)$_2$O— | | H | H | CH$_3$ | CH$_3$ | para-phenylene |
| 124 | —O(CH$_2$)$_2$O— | | H | H | CH$_3$ | C$_2$H$_5$ | para-phenylene |
| 125 | —O(CH$_2$)$_2$O— | | H | H | CH$_3$ | C$_3$H$_7^i$ | para-phenylene |
| 126 | —O(CH$_2$)$_2$O— | | H | H | C$_2$H$_5$ | C$_2$H$_5$ | para-phenylene |
| 127 | —O(CH$_2$)$_2$O— | | H | H | C$_2$H$_5$ | C$_3$H$_7^n$ | para-phenylene |
| 128 | CH$_3$ | CH$_3$ | H | —CCl$_2$— | | CH$_3$ | para-phenylene |
| 129 | *[fused bicyclic structure with OCH$_3$]* | | | | | | para-phenylene |

TABLE 4-continued

[Structure diagram: benzene ring with R11, R12, R13, R14, R15, R16 substituents and OCH linker, connected via O to pyridine/phenyl ring A with NH2]

| Compound No. | R11 | R12 | R13 | R14 | R15 | R16 | A |
|---|---|---|---|---|---|---|---|
| 130 | [spirocyclic structure with OCH3] | | | | | | [phenyl] |
| 131 | CH3 | CH3 | H | H | CH3 | OH | [phenyl] |

TABLE 5

[Structure diagram with R17, R18, R19, R20 substituents, O linker, ring A with NH2]

| Compound No. | R17 | R18 | R19 | R20 | A |
|---|---|---|---|---|---|
| 132 | CH3 | H | H | H | [pyridine N] |
| 133 | CH3 | H | H | H | [phenyl] |
| 134 | CH3 | CH3 | H | H | [pyridine N] |
| 135 | CH3 | CH3 | H | H | [phenyl] |
| 136 | H | H | CH3 | CH3 | [phenyl] |

TABLE 5-continued

| Compound No. | R17 | R18 | R19 | R20 | A |
|---|---|---|---|---|---|
| 137 | CH3 | OCH3 | H | H | [phenyl] |

TABLE 6

[Benzofuran structure with R21, R22 substituents, O linker, ring A with NH2]

| Compound No. | R21 | R22 | A |
|---|---|---|---|
| 138 | $C_3H_7^i$ | H | [phenyl] |

TABLE 6-continued
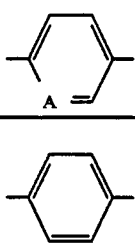
| Compound No. | $R^{21}$ | $R^{22}$ | A |
|---|---|---|---|
| 139 | $C_4H_9{}^i$ | H | 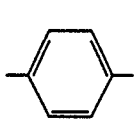 |
| 140 | H | $C_2H_5$ | 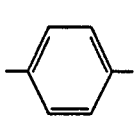 |
| 141 | H | $C_3H_7{}^n$ | 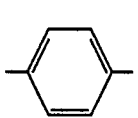 |
| 142 | H | $C_3H_7{}^i$ | |
TABLE 7
| Compound No. | $R^{23}$ | $R^{24}$ | $R^{25}$ | $R^{26}$ | A |
|---|---|---|---|---|---|
| 143 | H | H | $CH_3$ | H | 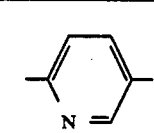 |
| 144 | H | H | $CH_3$ | H | 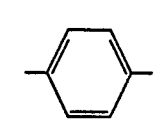 |
TABLE 8
| Compound No. | $R^{27}$ | $R^{28}$ | $R^{29}$ | A |
|---|---|---|---|---|
| 146 | H | $CH_3$ | $CH_3$ | |
TABLE 9
| Compound No. | $R^{30}$ | $R^{31}$ | A |
|---|---|---|---|
| 147 | $CH_3$ | $CH_3$ | |
TABLE 10
| Compound No. | $R^{32}$ | $R^{33}$ | $R^{34}$ | A |
|---|---|---|---|---|
| 148 | $CH_3$ | $CH_3$ | $CH_3$ | |
| 149 | $CH_3$ | $CH_3$ | $C_2H_5$ | |

TABLE 11

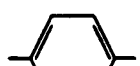

| Compound No. | $R^{35}$ | $R^{36}$ | $R^{37}$ | $R^{38}$ | A= |
|---|---|---|---|---|---|
| 150 | H | H | $CH_3$ | $CH_3$ | |
| 151 | H | H | $OCH_3$ | $CH_3$ | |
| 152 | H | $CH_3$ | $OCH_3$ | $CH_3$ | |

Preparation

The aromatic amine derivatives of the present invention may be prepared through a series of reactions as shown by the following formulae (1) and (2).

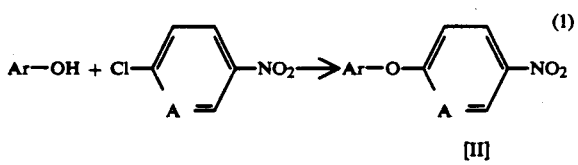 (1)

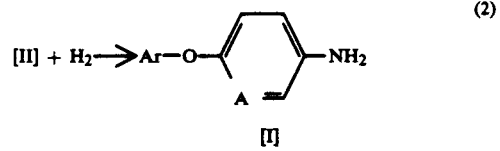 (2)

The reaction of formula (1) may be carried out by agitating the reagents in an aromatic hydrocarbon such as benzene, toluene, and xylene, an aprotic polar solvent such as N,N-dimethylformamide and 1-methyl-2-pyrrolidone, or a mixture thereof in the presence of a base such as NaOH, KOH, $Na_2CO_3$, $K_2CO_3$, NaH at a temperature of from 20° C. to 150° C. The reaction of formula (2) may proceed in a solvent inert to the reaction, for example, benzene, toluene, xylene, methanol, ethanol and ethyl acetate, in the presence of an ordinary reducing catalyst such as Raney nickel catalysts and palladium-carrying carbon under atmospheric pressure to a hydrogen pressure of 20 g/cm² at a temperature of from 20° C. to 100° C.

Among the compounds of general formula [II], those compounds represented by general formula [II-1]:

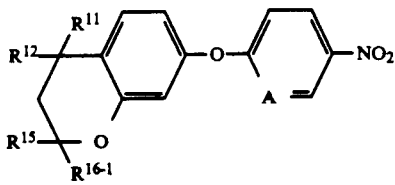 [II-1]

wherein $R^{11}$, $R^{12}$, $R^{13}$ and A are as defined above, $R^{16-1}$ is a lower alkoxy or hydroxyl radical can be produced not only by the reaction of formula (1), but also by a series of reactions as shown by formulae (3) and (4).

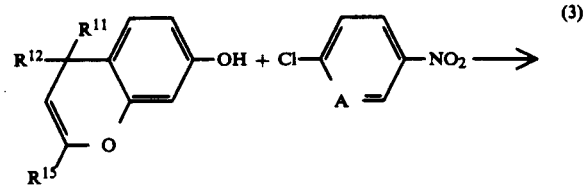 (3)

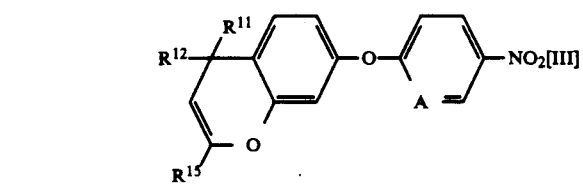

$$[III] + H - R^{16-1} \rightarrow [II-1] \quad (4)$$

The reaction of formula (3) may proceed under the same conditions as described for the reaction of formula (1). The reaction of formula (4) may be carried out without solvent or in an inert solvent such as acetone, dioxane, benzene and toluene in the presence of an acid catalyst such as HCl, $H_2SO_4$ and Amberlist-15 by heating to a temperature of from 40° C. to 120° C.

Among the compounds of general formula [II], those compounds represented by general formula [II-2]:

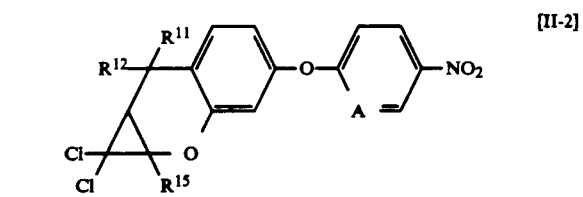 [II-2]

wherein $R^{11}$, $R^{12}$, $R^{15}$ and A are as defined above can be produced not only by the reaction of formula (1), but also by reaction as shown by formula (5).

$$[III] + :CCl_2 \rightarrow [II-2] \quad (5)$$

The reaction of formula (5) can be carried out by agitating a mixture of compound [III], chloroform, and NaOH or KOH without solvent or in an aqueous medium in the presence of a quaternary ammonium salt such as benzyltrimethyl ammonium chloride.

At the end of reaction, the end product can be recovered by a conventional method as shown in the following examples.

For typical ones of compounds Ar—OH used in the above preparation procedure, their typical synthesis is exemplified in Table 12 of Japanese Patent Application No. 61-177858 (WO 87/00840). Those compounds which are not exemplified in this Application may also be synthesized by a similar procedure.

EXAMPLES

Examples of the aromatic amine derivatives of the present invention are presented below by way of illustration and not by way of limitation.

Reference 1

Synthesis of 2-(3-methyl-2,3-dihydro-6-benzofuryloxy)-5-nitropyridine

A 50-ml two-necked round-bottomed flask equipped with a dropping funnel was charged with 0.64 grams of sodium hydride and washed twice with n-hexane. To the flask were added dropwise 2.0 grams of 3-methyl-2,3-dihydro-6-benzofuranol and 10 ml of dimethylformamide at room temperature. After evolution of hydrogen ceased, 2.1 grams of 2-chloro-5-nitropyridine in 10 ml of dimethylformamide was added dropwise. The mixture was agitated for 3 hours at room temperature. After water was added to the reaction mixture, the product was extracted with ethyl acetate, washed with water, and then dried over anhydrous magnesium sulfate. The extracting solvent was distilled off to leave a residue, which was purified by chromatography through a silica gel column using a 4/1 n-hexane/ethyl acetate mixture, obtaining 3.0 grams of brown crystals (yield 83%).

Melting point 99.0°–99.5° C.

IR spectrum (KBr disk; cm$^{-1}$) 3120, 3020, 2950, 1605, 1585, 1515, 1420, 1340, 1240, 998

$^1$H-NMR spectrum (CDCl$_3$ solution; ppm)

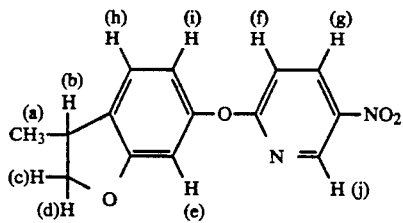

(a) 1.38 (3H, d, J=9.0Hz)
(b) 3.60 (1H, m)
(c) 4.18 (1H, t, J=8.1Hz)
(d) 4.78 (1H, t, J=8.1Hz)
(e) 6.63 (1H, d, J=3.6Hz)
(f) 7.05 (1H, d, J=9.0Hz)
(g) 7.50 (1H, d, J=3.6 and 9.0Hz)
(h) 7.63 (1H, d, J=7.2Hz)
(i) 7.68 (1H, dd, J=3.6 and 7.2Hz)
(j) 8.10 (1H, d, J=3.6Hz)

Reference 2

Synthesis of 4-(3-methyl-2,3-dihydro-6-benzofuryloxy)-nitrobenzene

A 50-ml two-necked round-bottomed flask equipped with a Dean-Stark apparatus and a condenser was charged with 2.0 grams of 3-methyl-2,3-dihydro-6-benzofuranol, 2.1 grams of 4-chloronitrobenzene, 1.1 grams of 85% potassium hydroxide, 5.0 ml of toluene, and 5.0 ml of dimethylformamide. The mixture was agitated for 2¼ hours at 140° C. while removing water formed. The reaction mixture was allowed to cool and then combined with water. The product was extracted with ethyl acetate, washed with water, and then dried over anhydrous magnesium sulfate. The extracting solvent was distilled off to leave a residue which was purified by chromatography through a silica gel column using a 4/1 n-hexane/ethyl acetate mixture, obtaining 3.1 grams of pale green crystals (yield 86%).

Melting point 90°–91° C.

IR spectrum (KBr disk; cm$^{-1}$) 3050, 2960, 1603, 1575, 1420, 1350, 1271, 1237, 1142, 997

$^1$H-NMR spectrum (CDCl$_3$ solution; ppm)

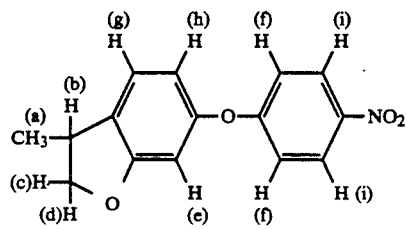

(a) 1.36 (3H, d, J=7.2Hz)
(b) 3.58 (1H, m)
(c) 4.18 (1H, t, J=9.0Hz)
(d) 4.78 (1H, t, J=9.0Hz)
(e) 6.55 (1H, d, J=2.7Hz)
(f) 7.05 (2H, d, J=9.0Hz)
(g) 7.18 (2H, d, J=9.0Hz)
(h) 7.60 (1H, d, J=7.2 and 9.0Hz)
(i) 8.22 (2H, dd, J=9.0Hz)

Example 1

Compound No. 1: 2-(3-methyl-2,3-dihydro-6-benzofuryloxy)-5-aminopyridine

In 20 ml of ethyl acetate was dissolved 2.0 grams of 2-(3-methyl-2,3-dihydro-6-benzofuryloxy)-5-nitropyridine. The solution was catalytically reduced in the presence of 0.2 grams of 5% palladium-carrying carbon at room temperature. After absorption of hydrogen ceased, the catalyst was filtered off and the filtrate was concentrated. The concentrate was purified was chromatography through a silica gel column using ethyl acetate solvent, obtaining 1.7 grams of the end product in the form of colorless liquid (yield 97%).

Mass spectrum m/z 242 (molecular ion peak)

IR spectrum (neat; cm$^{-1}$) 3400, 3050, 2950, 1602, 1357, 1271, 1235, 1130

$^{13}$H—NMR spectrum (CDCl$_3$ solution; ppm)

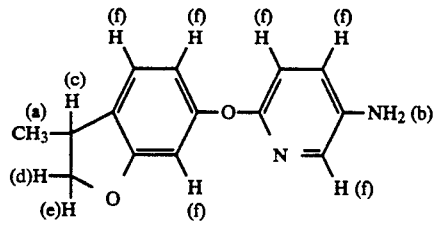

(a) 1.32 (3H, d, J=7.2Hz)
(b) 3.28 (2H ,brs)
(c) 3.24~3.72 (1H, m)
(d) 4.09 (1H, t, J=7.2Hz)
(e) 4.72 (1H, d, J=7.2Hz)
(f) 6.44~7.84 (6H, m)

Example 2

Compound No. 2:
4-(3-methyl-2,3-dihydro-6-benzofuryloxy)-aniline

The procedure of Example 1 was repeated except that the 2-(3-methyl-2,3-dihydro-6-benzofuryloxy)-5-nitropyridine was replaced by 4-(3-methyl-2,3-dihydro-6-benzofuryloxy)nitrobenzene. The reaction mixture was worked up in the same manner as in Example 1, obtaining the end product in the form of brown liquid (yield 98%).

Mass spectrum m/z 241 (molecular ion peak)

IR spectrum (neat; cm$^{-1}$) 3350, 3050, 2970, 1601, 1357, 1270, 1236, 1132

$^1$H—NMR spectrum (CDCl$_3$ solution; ppm)

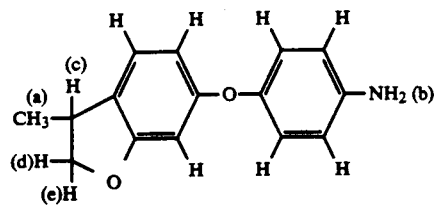

(a) 1.35 (3H, d, J=7.2Hz)
(b) 3.37 (2H, brs)
(c) 3.13~3.69 (1H, m)
(d) 4.09 (1H, t, J=7.2Hz)
(e) 4.70 (1H, t, J=7.2Hz)
(f) 6.32~7.18 (7H, m)

Compound Nos. 3 to 152 were synthesized by the same procedure as in Example 1. The results are summarized in Tabel 12. The yield was at least 95% for all the compounds.

TABLE 12

| Compound No. | As-produced | | Spectral analysis |
|---|---|---|---|
| 3 | viscous liquid | NMR: | 1.20(3H, d, J=8.1), 1.28(3H, s), 1.47(3H, s), 3.07(1H, q, J=8.1), 3.35(2H, brs), 6.24~8.00(6H, m). |
| 4 | viscous liquid | NMR: | 1.19(3H, d, J=9.0), 1.45(3H, s), 3.10(1H, q, J=9.0), 3.38(2H, brs), 6.28~7.10(7H, m). |
| 5 | viscous liquid | NMR: | 3.15(2H, t, J=7.2), 3.40(2H, brs), 4.60(2H, t, J=7.2), 6.20~7.40(7H, m). |
| 6 | viscous liquid | NMR: | 0.96(3H, t, J=7.2), 1.70(2H, q, J=7.2), 3.30(1H, m), 3.42(2H, brs), 4.24(1H, t, J=9.0), 4.65(1H, t, J=9.0), 6.30~7.50(7H, m). |
| 7 | viscous liquid | IR: | 3350($\nu_{NH}$), 3100, 2980, 1610, 1270, 1230. |
| 8 | viscous liquid | | |
| 9 | viscous liquid | NMR: | 1.46(3H, d, J=7.2), 2.74(1H, dd, J=8.0, 15.0), 3.27(1H, dd, J=8.0, 15.0), 3.52(2H, brs), 4.94(1H, m), 6.28~7.42(7H, m). |
| 10 | viscous liquid | NMR: | 1.04(3H, t, J=7.2), 1.76(2H, m), 2.78(1H, dd, J=8.0, 15.0), 3.22(1H, dd, J=8.0, 15.0), 3.55(2H, brs), 6.20~7.10(7H, m). |
| 11 | viscous liquid | NMR: | 0.98(3H, d, J=7.2), 1.06(3H, d, J=7.2), 1.89(1H, m), 2.85(1H, dd, J=8.0, 15.0), 3.14(1H, dd, J=8.0, 15.0), 3.48(2H, brs), 4.54(1H, m), 6.35~7.20(7H, m). |
| 12 | viscous liquid | NMR: | 0.93(3H, t, J=7.2), 1.00(3H, d, J=7.2), 1.61(3H, m), 2.70~3.30(2H, m), 3.42(2H, brs), 6.35~7.20(7H, m). |
| 13 | m.p. 86~87° C. | | |
| 14 | viscous liquid | NMR: | 0.95(3H, t, J=7.0), 1.40(3H, s), 1.74(2H, q, J=7.0), 2.95(2H, s), 3.42(2H, brs), 6.30~7.40(7H, m). |
| 15 | viscous liquid | NMR: | 0.91(6H, t, J=7.0), 1.70(4H, q, J=7.0), 2.95(2H, s), 3.46(2H, brs), 6.30~7.20(7H, m). |
| 16 | viscous liquid | NMR: | 0.90(3H, t, J=7.2), 1.14(3H, d, J=6.3), 1.17(3H, s), 1.70(2H, q, J=7.2), 3.08(1H, q, J=6.3), 3.30(2H, brs), 6.25~7.60(6H, m). |
| 17 | viscous liquid | NMR: | 0.98(3H, t, J=7.2), 1.20(3H, d, J=6.3), 1.24(3H, s), 1.75(2H, q, J=7.2), 3.10(1H, q, J=6.3), 3.45(2H, brs), 6.30~7.20(7H, m). |
| 18 | viscous liquid | NMR: | 0.99(3H, t, J=7.2), 1.22(3H, d, J=6.3), 1.24(3H, s), 1.78(2H, q, J=7.2), 3.18(1H, d, J=6.3), 3.52(2H, brs), 6.28~7.50(7H, m). |
| 19 | viscous liquid | IR: | 3400, 3320($\nu_{NH}$). |
| 20 | viscous liquid | IR: | 3410, 3310($\nu_{NH}$). |
| 21 | viscous liquid | NMR: | 1.26(3H, t, J=7.2), 1.34(3H, s), 1.46(3H, s), 1.63(2H, m), 2.84(1H, t, J=9.0), 3.36(2H, brs), 6.18~7.16(7H, m). |
| 22 | viscous liquid | | |
| 23 | viscous liquid | NMR: | 1.49(3H, d, J=6.3), 2.80~3.40(2H, m), 3.55(2H, brs), 4.90(1H, m), 6.24~7.62(6H, m). |
| 24 | m.p. 101~102° C. | | |
| 25 | viscous liquid | NMR: | 1.29(3H, d, J=6.9), 3.52(3H, m), 4.12(1H, t, J=9.0), 4.71(1H, t, J=9.0), 6.20~7.15(7H, m). |
| 26 | viscous liquid | NMR: | 0.94(3H, t, J=7.2), 1.70(2H, q, J=7.2), 3.44(3H, m), 4.21(1H, dd, J=9.0), 4.63(1H, t, J=9.0), 6.15~7.50(7H, m). |
| 27 | viscous liquid | NMR: | 0.96(3H, t, J=7.0), 1.24~1.78(4H, m), 3.10(1H, m), 3.42(2H, brs), 4.21(1H, dd, J=7.2, 9.0), 4.66(1H, t, J=9.0), 6.34~7.26(7H, m). |
| 28 | viscous liquid | | |
| 29 | viscous liquid | | |
| 30 | viscous liquid | NMR: | 0.97(3H, t, J=7.2), 1.36~1.90(2H, m), 2.90~3.20(1H, m), 3.50(2H, brs), 3.53(3H, s), 5.26(3H, d, J=2.7), 6.52~7.36(7H, m). |
| 31 | viscous liquid | | |
| 32 | m.p. 89.5~90.5° C. | | |
| 33 | viscous liquid | | |
| 35 | m.p. 94.5~95.5° C. | | |
| 36 | viscous liquid | | |
| 37 | viscous liquid | NMR: | 1.27(3H, s), 1.29(3H, s), 3.30(2H, brs), 3.56(3H, s), 5.13(1H, s), 6.50~7.80(6H, m). |
| 38 | viscous liquid | NMR: | 1.25(3H, s), 1.28(3H, s), 3.30(2H, brs), 3.56(3H, s), 5.11(1H, s), |

TABLE 12-continued

| Compound No. | As-produced | | Spectral analysis |
|---|---|---|---|
| | | | 6.48~7.00(7H, m). |
| 39 | viscous liquid | NMR: | 1.24(3H, s), 1.28(3H, s), 3.34(3H, s), 3.60(2H, brs), 5.10(1H, s), 6.40~6.90(6H, m). |
| 40 | viscous liquid | | |
| 41 | viscous liquid | | |
| 42 | viscous liquid | NMR: | 0.90(3H, d, J=6.4), 0.94(3H, d, J=6.4), 1.72~2.00(1H, m), 2.50~2.70(1H, m), 3.34(2H, brs), 5.32(3H, d, J=2.1), 6.40~7.20(7H, m). |
| 43 | viscous liquid | NMR: | 0.96(3H, t, J=7.7), 1.23(3H, t, J=7.1), 1.40~1.84(2H, m), 3.01~3.16(1H, m), 3.52~4.00(4H, m), 5.38(1H, d, J=2.1), 6.41~7.18(7H, m). |
| 44 | viscous liquid | NMR: | 0.88(3H, d, J=6.4), 0.92(3H, d, J=6.4), 1.24(3H, t, J=7.1), 1.80~2.12(1H, m), 3.02~3.12(1H, m), 3.52~4.06(4H, m), 5.44(1H, d, J =1.5), 6.40~7.18(4H, m). |
| 45 | viscous liquid | | |
| 46 | viscous liquid | | |
| 47 | viscous liquid | NMR: | 1.30~2.16(8H, m), 3.13~3.36(1H, m), 3.52(2H, brs), 4.64~4.88(1H, m), 6.32~7.41(7H, m). |
| 48 | viscous liquid | IR: | 3400($\nu_{NH}$), 3040, 2960, 1570, 1270, 1120. |
| 49 | viscous liquid | | |
| 50 | viscous liquid | NMR: | 3.48(2H, brs), 5.89(2H, s), 6.20~6.90(7H, m) |
| 51 | viscous liquid | NMR: | 1.01(3H, t, J=7.2), 1.61(3H, s), 1.95(2H, q, J=7.2), 3.40(2H, brs), 6.20~7.10(7H, m). |
| 52 | viscous liquid | | |
| 53 | viscous liquid | NMR: | 1.68(6H, s), 3.45(2H, brs), 6.20~7.10(7H, m). |
| 54 | viscous liquid | NMR: | 1.78(3H, s), 3.31(3H, s), 3.55(2H, brs), 6.30~7.00(7H, m). |
| 55 | viscous liquid | NMR: | 1.21(3H, t, J=7.2), 1.80(3H, s), 3.32(2H, brs), 3.61(2H, q, J=7.2), 6.30~7.08(7H, m). |
| 56 | viscous liquid | NMR: | 1.02(3H, t, J=7.2), 1.21(3H, t, J=7.2), 2.06(2H, q, J=7.2), 3.56(2H, q, J=7.2), 3.60(2H, brs), 6.30~7.00(7H, m). |
| 57 | viscous liquid | | |
| 58 | viscous liquid | | |
| 59 | viscous liquid | IR: | 3400($\nu_{NH}$), 3060, 2970 1603. |
| 60 | viscous liquid | | |
| 61 | viscous liquid | IR: | 3420($\nu_{NH}$), 3040, 2970, 1603, 1275. |
| 62 | viscous liquid | | |
| 63 | viscous liquid | IR: | 3400($\nu_{NH}$), 3060, 2955, 1605, 1275, 1238. |
| 64 | m.p. 109~110° C. | | |
| 65 | viscous liquid | NMR: | 1.38(3H, d, J=7.2), 1.60~2.00(2H, m), 2.64~2.94(2H, m), 3.37(2H, m), 6.40~7.80(6H, m). |
| 66 | viscous liquid | NMR: | 1.38(3H, d, J=9.0), 1.80(2H, m), 2.72(2H, m), 2.64(2H, brs), 4.16(1H, m), 6.40~7.80(6H, m). |
| 67 | m.p. 115.5~116.5° C. | | |
| 68 | m.p. 93~94° C. | NMR: | 1.30(6H, s), 1.76(2H, t, J=7.2), 2.72(2H, t, J=7.2), 3.38(2H, brs), 6.40~7.80(6H, m). |
| 69 | viscous liquid | NMR: | 1.30(6H, s), 1.77(2H, t, J=7.2), 2.72(2H, t, J=7.2), 3.44(2H, brs), 6.20~7.18(7H, m). |
| 70 | viscous liquid | NMR: | 1.32(6H, s), 1.78(2H, t, J=7.2), 2.72(2H, t, J=7.2), 3.64(2H, brs), 6.20~7.10(6H, m). |
| 71 | viscous liquid | IR: | 3420($\nu_{NH}$), 3040, 2970, 1605, 1535, 1370. |
| 72 | viscous liquid | | |
| 73 | viscous liquid | NMR: | 1.29(3H, s), 1.32(3H, d, J=7.2), 1.62(1H, s), 1.68(1H, s), 3.28(2H, brs), 4.16(1H, q, J=7.2), 6.40~7.80(6H, m). |
| 74 | viscous liquid | | |
| 75 | viscous liquid | IR: | 3380($\nu_{NH}$), 3180, 3040, 2960, 1605, 1275. |
| 76 | viscous liquid | IR: | 3410($\nu_{NH}$), 3060, 2970, 1610, 1270, 1235, 1140. |
| 77 | viscous liquid | NMR: | 1.32(3H, s), 1.41(3H, s), 1.99(1H, d, J=7.2), 2.03(1H, d, J=7.2), 3.44(3H, s), 3.50(2H, brs), 4.38(1H, t, J=7.2), 6.20~7.40(7H, m). |
| 78 | m.p. 104.5~105.5° C. | | |
| 79 | viscous liquid | NMR: | 1.26(3H, s), 1.41(3H, s), 1.49(3H, s), 1.81(1H, d, J=14.0), 1.95(1H, d, J=14.0), 2.65(2H, brs), 3.23(3H, s), 6.40~7.30(7H, m). |
| 80 | viscous liquid | NMR: | 1.25(3H, s), 1.41(3H, s), 1.48(3H, s), 1.80(1H, d, J=14.4), 2.02(1H, d, J=14.4), 3.21(3H, s), 3.64(2H, brs), 6.20~7.32(7H, m). |
| 81 | viscous liquid | IR: | 3410($\nu_{NH}$), 3330($\nu_{NH}$), 1610, 1524, 1470, 1350, 1265, 1230. |
| 82 | viscous liquid | | |
| 83 | viscous liquid | NMR: | 1.00(3H, t, J=7.2), 1.26(3H, s), 1.44(3H, s), 1.50(3H, s), 1.88(1H, d, J=14.0), 1.95(1H, d, J=14.0), 3.35(2H, brs), 3.55(2H, q, J=7.2), 6.32~7.30(7H, m). |
| 84 | viscous liquid | NMR: | 0.72(3H, t, J=7.2), 1.20~1.60(2H, m), 1.28(3H, s), 1.46(3H, s), 1.54(3H, s), 1.84(1H, d, J=13.5), 2.05(1H, d, J=13.5), 3.47(4H, m), 6.20~7.20(7H, m). |
| 85 | viscous liquid | NMR: | 0.84, 1.11(total 6H, d, J=7.2), 1.25(3H, s), 1.45(3H, s), 1.51(3H, s), 1.74(1H, d, J=13.5), 1.99(1H, d, J=13.5), 3.56(2H, brs), 4.12(1H, m), 6.30~7.26(7H, m). |
| 86 | viscous liquid | NMR: | 1.82~2.20(2H, m), 3.43(3H, s), 3.48(2H, brs), 4.10~4.36(3H, m), 6.30~7.35(7H, m). |
| 87 | viscous liquid | NMR: | 1.00(3H, t, J=7.2), 1.40~2.16(4H, m), 2.50~3.00(2H, m), 3.50(2H, brs), 3.70~4.04(1H, m), 6.20~7.33(7H, m). |
| 88 | viscous liquid | | |
| 89 | viscous liquid | NMR: | 1.90(2H, m), 2.56(2H, m), 3.40(3H, s), 3.52(2H, brs), 5.01(1H, t, J=1.8), 6.18~7.31(7H, m). |
| 90 | viscous liquid | | |
| 91 | viscous liquid | NMR: | 1.00(3H, t, J=7.2), 1.80(4H, m), 2.60(1H, m), 3.48(2H, brs), 4.16(2H, t, J=5.4), 6.10~7.15(7H, m). |

TABLE 12-continued

| Compound No. | As-produced | Spectral analysis |
|---|---|---|
| 92 | viscous liquid | NMR: 0.97(3H, d, J=7.2), 1.18(3H, d, J=7.2), 2.00~2.10(1H, m), 2.72~3.04(1H, m), 3.48(2H, brs), 3.78~4.20(2H, m), 6.30~7.10(7H, m). |
| 93 | viscous liquid | |
| 94 | viscous liquid | NMR: 1.30, 1.35(total 3H, d, J=7.2), 1.60~2.28(2H, m), 2.94(1H, m), 3.47, 3.51(total 3H, s), 3.49(2H, brs), 6.30~7.42(7H, m). |
| 95 | viscous liquid | NMR: 1.00~1.50(6H, m), 1.60~2.28(2H, m), 3.08(1H, m), 3.24~4.08(4H, m), 5.20(1H, dd, J=3.6, 7.2), 6.32~7.46(7H, m). |
| 96 | viscous liquid | NMR: 1.40(3H, d, J=7.2), 1.62~2.44(2H, m), 3.44(3H, s), 3.54(2H, brs), 4.20(1H, m), 4.56(1H, dd, J=6.3, 10.8), 6.21~7.32(7H, m). |
| 97 | viscous liquid | |
| 98 | viscous liquid | NMR: 0.96(3H, d, J=7.2), 1.26(3H, d, J=7.2), 2.00~3.08(3H, m), 3.48(2H, m), 4.08~4.18(1H, m), 6.33~7.20(7H, m). |
| 99 | viscous liquid | NMR: 0.82~1.12(6H, m), 1.20~1.81(3H, m), 2.20~2.80(2H, m), 3.48(2H, brs), 4.10(1H, m), 6.24~7.26(7H, m). |
| 100 | viscous liquid | |
| 101 | viscous liquid | IR: 3420($\nu_{NH}$), 3070, 2940, 1570, 1275, 1238. |
| 102 | viscous liquid | IR: 3420($\nu_{NH}$), 3050, 2955, 1610, 1570, 1575, 1240. |
| 103 | viscous liquid | |
| 104 | m.p. 85~86° C. | NMR: 0.89(6H, t, J=7.2), 1.25~1.67(6H, m), 1.78(2H, t, J=7.2), 2.68(2H, t, J=7.2), 3.48(2H, brs), 6.32~7.22(7H, m). |
| 105 | viscous liquid | |
| 106 | viscous liquid | NMR: 1.55(3H, s), 1.64~2.24(2H, m), 2.36~3.04(2H, m), 3.28(2H, brs), 3.30(3H, s), 6.36~7.10(7H, m). |
| 107 | viscous liquid | NMR: 1.04(3H, t, J=7.2), 1.58(3H, s), 1.70~2.28(2H, m), 2.60~3.24(2H, m), 3.48(2H, brs), 3.62(2H, q, J=7.2), 6.36~7.40(7H, m). |
| 108 | viscous liquid | NMR: 0.85(3H, t, J=7.2), 1.14(3H, t, J=7.2), 1.54(3H, s), 1.66~2.24(2H, m), 2.40~2.80(2H, m), 3.49(2H, brs), 4.22(1H, m), 6.26~7.38(7H, m). |
| 109 | viscous liquid | NMR: 0.95(3H, t, J=7.2), 1.50~2.20(4H, m), 2.40~3.00(2H, m), 3.24(3H, s), 3.38(2H, brs), 6.36~7.08(7H, m). |
| 110 | viscous liquid | |
| 111 | viscous liquid | |
| 112 | viscous liquid | NMR: 1.08(3H, d, J=7.2), 1.40(3H, d, J=7.2), 1.60~2.00(1H, m), 3.31(3H, s), 3.51(2H, brs), 3.80~4.26(2H, m), 6.20~7.40(7H, m). |
| 113 | viscous liquid | NMR: 0.99(3H, d, J=7.2), 1.14(3H, s), 1.35(3H, s), 1.62~2.10(1H, m), 2.30~2.88(2H, m), 3.47(2H, brs), 6.30~7.12(7H, m). |
| 114 | viscous liquid | NMR: 1.08(3H, d, J=7.2), 1.49(3H, s), 1.98(1H, m), 2.46~2.76(2H, m), 3.23(3H, s), 3.42(2H, brs), 6.20~7.12(7H, m). |
| 115 | viscous liquid | NMR: 0.94(3H, t, J=7.2), 1.25 and 1.36(total 3H, s), 1.50~1.76(2H, m), 1.81~2.12(2H, m), 3.44 and 3.46(total 3H, s), 3.54(2H, brs), 4.41(1H, brs), 6.24~7.30(7H, m). |
| 116 | viscous liquid | |
| 117 | viscous liquid | NMR: 0.89(6H, t, J=7.2), 1.50~2.10(6H, m), 3.44(3H, s), 3.50(2H, brs), 4.37(1H, t, J=6.3), 6.20~7.40(7H, m). |
| 118 | viscous liquid | NMR: 0.90(6H, t, J=7.2), 1.10~2.20(8H, m), 3.46(3H, s), 3.52(2H, brs), 4.38(1H, t, J=7.2), 6.30~7.40(7H, m). |
| 119 | viscous liquid | |
| 120 | viscous liquid | NMR: 1.04(3H, t, J=7.2), 1.52~2.14(4H, m), 3.42(3H, brs), 3.92~4.40(5H, m), 6.20~7.20(7H, m). |
| 121 | viscous liquid | NMR: 1.00(6H, d, J=6.3), 1.85~1.94(3H, m), 3.47(2H, brs), 4.04(1H, m), 4.15(4H, m), 6.30~7.32(7H, m). |
| 122 | viscous liquid | NMR: 0.97(3H, d, J=7.0), 1.38(3H, d, J=7.0), 2.12(1H, m), 3.50(2H, brs), 4.09~4.35(5H, m), 6.33~7.18(7H, m). |
| 123 | viscous liquid | NMR: 1.42(6H, s), 2.13(2H, s), 3.50(2H, brs), 4.00~4.30(4H, m), 6.24~7.14(7H, m). |
| 124 | viscous liquid | NMR: 0.92(3H, t, J=7.0), 1.34(3H, s), 1.70(2H, q, J=7.2), 2.01(1H, d, J=14.4), 2.20(1H, d, J=14.4), 3.20(2H, brs), 4.00~4.30(4H, m), 6.30~7.44(7H, m). |
| 125 | viscous liquid | |
| 126 | viscous liquid | NMR: 0.87(6H, t, J=7.2), 1.68(4H, q, J=7.2), 2.10(2H, s), 3.42(2H, brs), 4.00~4.30(4H, m), 6.22~7.20(7H, m). |
| 127 | viscous liquid | NMR: 0.88(6H, t, J=7.2), 1.10~1.50(2H, m), 1.69(4H, q, J=7.2), 2.09(2H, s), 3.49(2H, brs), 3.90~4.30(4H, m), 6.18~7.10(7H, m). |
| 128 | viscous liquid | NMR: 1.36(3H, s), 1.62(3H, s), 1.68(1H, s), 1.80(3H, s), 3.54(2H, brs), 6.20~7.18(7H, m). |
| 129 | viscous liquid | NMR: 1.80~2.24(6H, m), 3.06(1H, m), 3.53(3H, s), 3.55(2H, brs), 6.32~7.22(7H, m). |
| 130 | viscous liquid | NMR: 1.40~1.92(6H, m), 2.00~2.30(2H, m), 3.18(1H, m), 3.50(2H, brs), 3.76(3H, s), 6.18~7.32(7H, m). |
| 131 | m.p. 140.0~141.0 | IR: 3385, 3320($\nu_{NH}$), 3040($\nu_{NH}$), 1610, 1578, 1498, 1208, 1132, 1162, 990.<br>NMR: 1.31(3H, s), 1.47(3H, s), 1.60(3H, s), 1.82(1H, d, J=13.5), 2.04(1H, d, J=13.5), 3.12(2H, brs), 6.35(1H, d, J=2.7), 6.55(1H, dd, J=2.7, 9.0), 6.65(2H, d, J=9.0), 6.89(2H, d, J=9.0), 7.20(1H, d, J=9.0). |
| 132 | viscous liquid | NMR: 1.40(3H, d, J=7.2), 1.80(2H, m), 2.74(2H, m), 3.48(2H, brs), 4.12(1H, m), 6.60~7.84(6H, m). |
| 133 | viscous liquid | NMR: 1.38(2H, d, J=7.2), 1.80(2H, m), 2.70(2H, m), 3.52(2H, brs), 4.11(1H, m), 6.53~6.96(7H, m). |
| 134 | viscous liquid | NMR: 1.33(6H, s), 1.78(2H, t, J=7.2), 2.75(2H, t, J=7.2), 3.25(2H, brs), 6.60~7.80(6H, m). |
| 135 | viscous liquid | |
| 136 | viscous liquid | |
| 137 | viscous liquid | NMR: 1.55(3H, s), 1.66~2.21(2H, m), 2.32~3.10(2H, m), 3.22(2H, brs), 3.30(3H, s), 6.50~7.00(7H, m). |

TABLE 12-continued

| Compound No. | As-produced | Spectral analysis | |
|---|---|---|---|
| 138 | viscous liquid | NMR: | 1.35(6H, d, J=6.9), 2.98~3.10(1H, m), 3.48(2H, brs), 6.36(1H, s), 6.30~7.32(7H, m). |
| 139 | viscous liquid | NMR: | 0.98(3H, d, J=6.9), 1.02(3H, d, J=6.9), 1.90~2.28(1H, m), 2.64(2H, dd, J=2.7, 6.7), 3.47(2H, brs), 6.32(1H, s), 6.34~7.18(7H, m). |
| 140 | viscous liquid | NMR: | 1.30(3H, t, J=7.7), 2.64(2H, q, J=7.7), 6.32~7.34(8H, m). |
| 141 | viscous liquid | NMR: | 0.80~1.84(5H, m), 1.56(2H, t, J=7.7), 3.50(2H, brs), 6.20~7.40(8H, m). |
| 142 | viscous liquid | NMR: | 1.30(6H, d, J=6.7), 2.90~3.14(1H, m), 3.47(2H, brs), 6.20~7.35(8H, m). |
| 143 | viscous liquid | NMR: | 1.42(3H, d, J=6.3), 2.84(1H, dd, J=7.2, 14.4), 2.96(1H, dd, J=7.2, 14.4), 3.56(2H, brs), 4.92(1H, m), 6.20~7.60(6H, m). |
| 144 | viscous liquid | NMR: | 1.48(3H, d, J=6.4), 2.88(1H, dd, J=7.7, 15.4), 3.38(1H, dd, J=7.7, 15.4), 3.52(2H, brs), 5.00(1H, m), 6.38~7.32(8H, m). |
| 146 | viscous liquid | NMR: | 1.26(6H, s), 1.80(2H, t, J=7.1), 2.82(2H, t, J=7.1), 3.52(2H, brs), 6.33~7.10(7H, m). |
| 147 | viscous liquid | | |
| 148 | viscous liquid | NMR: | 1.19(3H, d, J=7.2), 1.37(3H, s), 1.40(3H, s), 2.24(3H, s), 3.10(1H, q, J=7.2), 3.48(2H, brs), 6.20~7.20(6H, m). |
| 149 | viscous liquid | NMR: | 0.92(3H, t, J=7.2), 1.18(3H, d, J=6.3), 1.30(3H, s), 1.68(2H, q, J=7.2), 2.20(3H, s), 3.12(1H, q, J=6.3), 3.52(2H, brs), 6.30~7.22(6H, m). |
| 150 | viscous liquid | NMR: | 1.30(3H, s), 1.82(2H, t, J=6.7), 2.16(3H, s), 2.60(2H, t, J=6.7), 3.52(2H, brs), 6.20~7.12(6H, m). |
| 151 | viscous liquid | | |
| 152 | viscous liquid | NMR: | 1.16(3H, d, J=7.2), 1.52(3H, s), 1.80~2.12(1H, m), 2.22(3H, s), 2.44(2H, d, J=9.0), 3.24(3H, s), 3.48(2H, brs), 6.24~7.42(6H, m). |

The aromatic amine derivatives of the present invention are useful as intermediates for herbicides.

More particularly, compounds of general formula [IV]:

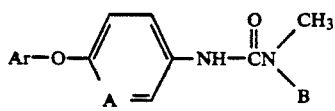

wherein Ar and A are as defined above, and B is a hydrogen atom, a methyl or methoxy radical can be produced from the aromatic amine derivatives of the present invention by the method described in Japanese Patent Application No. 61-177858 (WO 87/00840) which is assigned to the same assignee as the present invention and whose disclosure is incorporated herein by reference. The compounds of formula [IV] are effective as herbicides as described in Japanese Patent Application No. 61-177858 (WO 87/00840). The specification of the Application reports the measured physical properties of the compounds, to which the measured physical properties of the aromatic amine derivatives of the present invention conform.

We claim:

1. An aromatic amine compound of the formula (I):

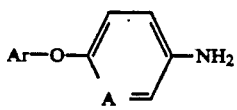

wherein Ar is a radical selected from the group consisting of

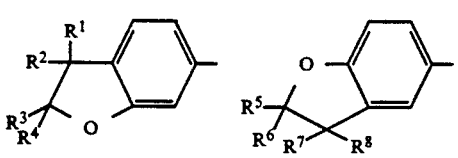

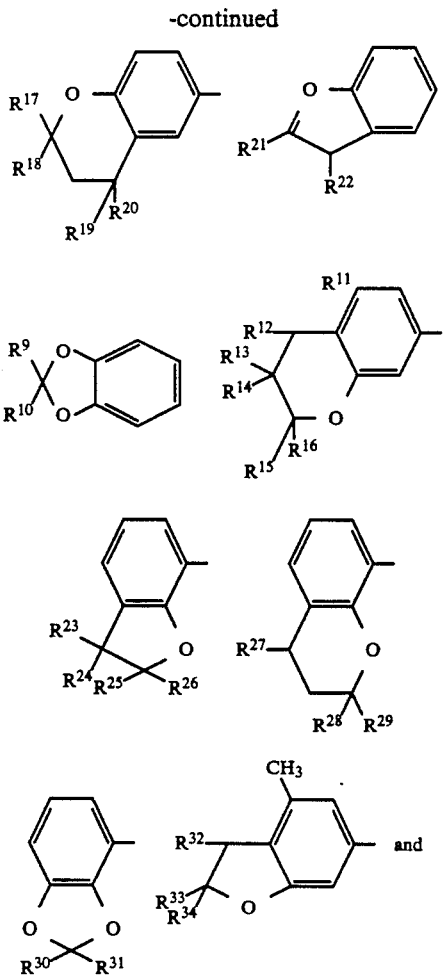

-continued

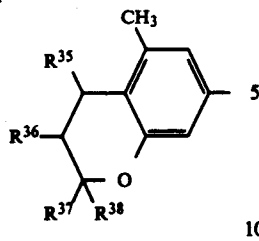

wherein $R^1$ to $R^{15}$ and $R^{17}$ to $R^{38}$ may be the same or different and are independently selected from the group consisting of hydrogen, lower alkyl radicals, and lower alkoxy radicals, $R^{16}$ is selected from the group consisting of hydrogen, lower alkyl radicals, lower alkoxy radicals and hydroxyl, with the proviso that $R^2$ and $R^3$, $R^6$ and $R^7$, $R^9$ and $R^{10}$, $R^{11}$ and $R^{15}$, or $R^{15}$ and $R^{16}$ may, taken together, represent an alkylene chain, which may be substituted with a lower alkyl radical, to form a 5- or 6-membered ring with the carbon atoms to which they are attached, $R^{11}$ and $R^{12}$ may, taken together, represent an ethylene dioxyl radical, or $R^{14}$ and $R^{15}$ may, taken together, represent a dichloromethylene radical; and A is

wherein X is a nitro radical.

* * * * *

UNITED STATES PATENT AND TRADEMARK OFFICE
CERTIFICATE OF CORRECTION

PATENT NO. : 5,011,950

DATED : April 30, 1991

INVENTOR(S) : DAISUKE FUKUOKA; KATSUYA TAKAHASHI; and ISAO HASHIMOTO

It is certified that error appears in the above-identified patent and that said Letters Patent is hereby corrected as shown below:

Column 1, line 11, change "fields" to --yields--;
Column 1, line 17, change "search" to --research--;

Column 15, directly below "TABLE 2"; Column 16, directly below "TABLE 2-continued"; Column 17, directly below "TABLE 2-continued"; and Column 18, directly below "TABLE 2-continued", change the formula to read as follows:

Table 2

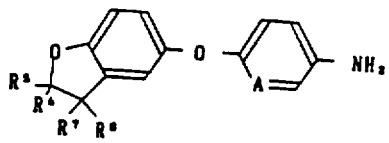

Column 40, line 30, change "(i) 8.22(2H,dd,J=9.0Hz)" to
              --(i) 8.22(2H,d,J=9.0Hz)--;
Column 40, line 44, change "was" (second occurrence) to --by--;
Column 40, line 51, change "$^{13}$H-NMR" to -- $^{1}$H-NMR--.
Column 40, line 66, change "(e)4.72(1H,d,J=7.2Hz)" to --(e)4.72(1H,t,J=7.2Hz)

Columns 41 & 42, Compound No. 26, change "4.21(1H,dd,J=9.0)" to
              --4.21(1H,dd,J=7.2,9.0)--

UNITED STATES PATENT AND TRADEMARK OFFICE
CERTIFICATE OF CORRECTION

PATENT NO. : 5,011,950

DATED : April 30, 1991

INVENTOR(S) : Daisuke Fukuoka; Katsuya Takahashi; and Isao Hashimoto

It is certified that error appears in the above-identified patent and that said Letters Patent is hereby corrected as shown below:

Column 45 & 46, Compound No. 112, change "3.80~4.26 (2H,m)" to --3.80~4.36 (2H,m)--;

Column 45 & 46, Compound No.133, change "6.53~6.96(7H,m)" to -- 6.52~6.96(7H,m)--

Signed and Sealed this

Eighth Day of December, 1992

Attest:

DOUGLAS B. COMER

Attesting Officer

Acting Commissioner of Patents and Trademarks